(12) United States Patent
Souppe et al.

(10) Patent No.: US 7,083,816 B2
(45) Date of Patent: Aug. 1, 2006

(54) MODIFIED WHEY, METHOD FOR PREPARING SAME, USE AND BREAD-MAKING PRODUCT COMPRISING MODIFIED WHEY

(75) Inventors: Jerome Souppe, Rennes (FR); Joel Prodhomme, Margueray (FR)

(73) Assignee: Compagnie Laitiere Europeenne, Conde sur Vire (FR)

( * ) Notice: Subject to any disclaimer, the term of this patent is extended or adjusted under 35 U.S.C. 154(b) by 319 days.

(21) Appl. No.: 10/484,263

(22) PCT Filed: Jul. 15, 2002

(86) PCT No.: PCT/FR02/02510

§ 371 (c)(1),
(2), (4) Date: Jan. 20, 2004

(87) PCT Pub. No.: WO03/007731

PCT Pub. Date: Jan. 30, 2003

(65) Prior Publication Data

US 2004/0161493 A1    Aug. 19, 2004

(30) Foreign Application Priority Data

Jul. 17, 2001    (FR) .................................. 01 09518

(51) Int. Cl.
*A23C 21/02* (2006.01)
*A23J 3/08* (2006.01)
*A21D 13/06* (2006.01)

(52) U.S. Cl. ........................ 426/41; 426/42; 426/549; 426/583

(58) Field of Classification Search .................. 426/41, 426/42, 549, 583
See application file for complete search history.

(56) References Cited

U.S. PATENT DOCUMENTS

| | | | | |
|---|---|---|---|---|
| 4,358,464 A | * | 11/1982 | Soehnlen | 426/41 |
| 4,500,549 A | * | 2/1985 | Crossman | 426/33 |
| 4,522,832 A | * | 6/1985 | Morrison | 426/20 |
| 4,614,653 A | * | 9/1986 | Kakade | 426/2 |
| 4,622,300 A | * | 11/1986 | Ottofrickenstein et al. | 435/105 |
| 5,039,532 A | * | 8/1991 | Jost et al. | 426/41 |
| 5,176,928 A | * | 1/1993 | Shazer et al. | 426/42 |
| 5,618,689 A | * | 4/1997 | McCarthy et al. | 435/68.1 |
| 5,952,193 A | | 9/1999 | Kawaguchi et al. | |
| 6,288,222 B1 | * | 9/2001 | Roth et al. | 536/127 |
| 6,372,282 B1 | * | 4/2002 | Edens et al. | 426/656 |
| 6,720,018 B1 | * | 4/2004 | Kawachi et al. | 426/422 |
| 6,833,260 B1 | * | 12/2004 | Ruch | 435/207 |
| 6,863,918 B1 | * | 3/2005 | Bindels et al. | 426/590 |

FOREIGN PATENT DOCUMENTS

| | | | |
|---|---|---|---|
| GB | 2 139 071 | | 11/1984 |
| JP | 7-313174 | * | 12/1995 |
| SU | 1242098 | * | 7/1986 |
| WO | 99 65326 | | 12/1999 |

OTHER PUBLICATIONS

Wong et al. "Lactose", Fundamentals of Dairy Chemistry. Third edition. p. 309-315 & 323-328. Pub. 1999.*

* cited by examiner

*Primary Examiner*—Keith Hendricks
(74) *Attorney, Agent, or Firm*—Oblon, Spivak, McClelland, Maier & Neustadt, P.C.

(57) ABSTRACT

The invention concerns a method for preparing modified whey comprising steps which consists in: a) lactose removal, b) hydrolysis, c) pre-treatment of calcium trap proteins, d) hydrolysis of the pre-treated proteins and e) enzyme inactivation. The hydrolysis process is carried out in the presence of at least an endopeptidase and of at least an exopeptidase. The invention also concerns whey obtainable by said preparation method characterised in that it comprises a lactose content between 10 and 50 wt. % of the weight initially present and an amount of total proteins representing not more than 80 wt. % of the weight of proteins initially present. The invention further concerns the use of said modified whey as bread-making enhancing agent and products containing same.

27 Claims, 2 Drawing Sheets

*Conversion of whey to a bread improver*

*Conversion of whey to a bread improver*

MODIFIED WHEY, METHOD FOR PREPARING SAME, USE AND BREAD-MAKING PRODUCT COMPRISING MODIFIED WHEY

The present invention relates to a modified whey, its method of preparation, its application in the field of bread products and the bread products comprising said modified whey.

The staling of bread is essentially due to the retrogradation of starch, which results from the formation of hydrogen bonds between the hydroxyl groups of the glucose residues of starch. Thus, industrial bread products, such as sandwich bread, brioches-type bread, genoese, French country bread or Vienna-type products harden rapidly.

Various solutions have been proposed for overcoming this problem:

- the accelerated rotation of the products on shelves, which requires working with a tight turnover, with fairly cumbersome logistical constraints;
- the use of additives such as emulsifiers (distilled monoglycerides, acetylated tartaric acid esters (DATA), and the like) or water retaining agents (guar and xanthan gums, and the like). These products must be mentioned in the list of ingredients, which is generally poorly viewed by consumers;
- the use of technological aids of an enzymatic nature. The most effective product to date is a maltogenic and thermostable amylase, produced by NOVO NORDISK and whose trade name is "NOVAMYL®".

This enzyme has a number of disadvantages:
- it makes it possible to delay the staling of industrial bread products by only 8 to 10 days according to the products,
- its high cost limits its use
- this enzyme is not active in Vienna-type products, and
- it is derived from a genetically modified microorganism.

This problem of staling is therefore not currently satisfactorily resolved.

That is why the applicant has set itself the aim of providing an effective solution to this problem of staling of industrial bread products.

The applicant has thus surprisingly found a solution to this problem of staling of industrial bread products by incorporating modified whey into said products.

Whey is the residual liquid obtained after extracting proteins and fat from milk. Two categories of whey are distinguishable according to whether its acidity is less than or greater than 1.8 g of lactic acid/l: sweet whey, derived from the manufacture of cooked or uncooked pressed cheese (emmenthal, saint-paulin, and the like) and acid whey, derived from other cheeses obtained by mixed or lactic coagulation (soft cheeses, fromage frais). The average composition of sweet whey is, as a guide, for 61 g of dry matter per kg of whey, from 42 to 48 g of lactose, 8 g of proteins, 2 g of fat, 5 to 7 g of minerals, 1 to 5 g of lactic acid and the remainder as minerals and vitamins.

The expression "initial whey" is understood to mean whey as defined above. Sweet wheys are preferred since they are easier to dry.

The subject of the present invention is therefore a method for preparing modified whey, characterized in that it comprises the following steps:

a) removal of lactose from an initial whey by evaporation of the whey, so as to crystallize the lactose in alfamonohydrate form which can be easily separated; preferably, a concentrated whey is thus obtained comprising from 55 to 70% dry matter, b) hydrolysis of the whey obtained in step a) with the aid of lactases, preferably at a pH between 3 and 7 and at a temperature $\leq 40°$ C., until a lactose level between 10 and 50% by weight of the quantity of lactose initially present in the unmodified initial whey is obtained; advantageously, during this step, the lactose is predominantly converted to glucose and to galactose; preferably, a lactose level of 10 to 35%, preferably of 35% by weight of the quantity of lactose initially present in the unmodified initial whey is obtained in this step b), c) pretreatment of the proteins contained in the whey obtained in step b) by adding a calcium trap to said whey, in the hot state and at a substantially neutral pH, d) hydrolysis, in the hot state, of the pretreated proteins in step c) in the presence of at least one endopeptidase, at least one exopeptidase and at least one molecule capable of cutting the disulfide bridges until a level of total proteins representing at most 80% by weight of the initial weight of proteins present in the unmodified initial whey is obtained; a level of hydrolysis preferably of between 20 and 25% is obtained, and e) inactivation of all the enzymes present in the whey obtained in step d).

Preferably:

the lactose removal according to step a) is carried out in accordance with techniques well known to the person skilled in the art and preferably comprises concentration by evaporation, followed by drying.

the hydrolysis according to step b) is carried out in the presence of an acid lactase which has an optimum activity at a pH of between 3 and 5, preferably at a pH of 4 or of a neutral lactase which has an optimal activity at a pH of between 5 and 7, preferably at a pH of 6.3, preferably at 37° C.; also preferably, the quantity of lactase is from 0.1 to 0.5 g per 100 g of dry extract (or dry matter). The hydrolysis of the lactose is advantageously continued until a level of hydrolysis of the lactose of at least 50% and preferably of 65 to 90% is obtained: a lactose level of 10 to 35%, preferably of 35% of the quantity of lactose initially present in the unmodified whey is thus obtained. The level of hydrolysis is measured by assaying the free sugars, in particular the glucose by glucometry.

the pretreatment of the proteins according to step c) is preferably carried out at a temperature between 40° C. and 50° C. and at a pH between 6.5 and 7.5, preferably at pH 7. At this stage, the calcium trap, preferably present in a quantity of 1% dry extract, is selected from the group consisting of disodium citrate, sodium lactate and certain polyphosphates.

the hydrolysis of the proteins according to step d) is advantageously carried out at a temperature between 35° C. and 60° C., preferably 45° C., in the presence:

of an endopeptidase selected from the group consisting of a neutrase, in particular the neutrase marketed by NOVO, pancreatin, delvolase or alkaline protease derived from *Bacillus licheniformis,* papain or protease V100 and a neutral protease from the genus *Aspergillus* (*niger, oryzae, sojae, melleus* or *wentii.* of a fungal exopeptidase, preferably of the genus *Aspergillus* (*niger, oryzae, sojae, melleus, wentii*) and of a molecule capable of cutting the disulfide bridges, selected from the group consisting of sodium metabisulfite, cysteine or a glutathion-rich yeast extract. Sodium metabisulfite destroys the tertiary structure of the proteins; in addition, it makes it possible to maintain a redox potential at the site, necessary for example for the activity of papain. The level of hydrolysis of the proteins is measured by assaying the freed $NH_2$ or COOH groups.

the inactivation of all the enzymes in step e) is carried out since, in order for the enzymes to be considered as technological aids, in accordance with the regulations, they must be inactive.

According to an advantageous embodiment of said method, the temperature and the duration of step e) depend on the enzymatic cocktail used; the conditions are in particular 90° C. for 30 minutes.

The method of preparing modified whey according to the invention may comprise one or more additional steps which make it possible to concentrate the modified whey obtained in step e).

According to another advantageous embodiment of the method of preparing whey, it comprises an additional step f) of concentrating the modified whey obtained in step e) in order to obtain a concentrate containing 50–60% dry extract, preferably 55%.

The subject of the present invention is also a modified whey which can be obtained by the method described above and characterized in that it comprises a quantity of lactose between 10 and 50% by weight of the quantity by weight initially present and a quantity of proteins representing at most 80% by weight of the quantity by weight of proteins initially present.

The modified whey according to the invention may be provided in liquid form, in the form of a concentrate or of a dry powder.

For cost of transportation reasons, the whey will be preferred in the form of a concentrate containing 50 to 70% dry extract, preferably 55% dry extract.

This modified whey according to the invention has the following advantages:

it makes it possible to significantly slow the staling of industrial bread products containing it compared with bread products not containing it.

the modified whey according to the invention, when added to the abovementioned bread products, makes it possible to reduce up to ten times the dose of NOVAMYL® in the flour, or even to avoid the addition of NOVAMYL® to the flour; in the latter case, for a result at least as good in terms of slowing staling of the bread products; that constitutes an advantageous reduction in cost for the bread-making industrialist since these products do not contain a large quantity of expensive ingredients;

it additionally allows good enhancement of the value of the lactose-free whey for the manufacturer of lactose.

Surprisingly, the applicant has also observed that the use of whey according to the invention made it possible to obtain the following advantages in the preparation of a bread product:

production of a bread dough with improved smoothness, all else being equal. The prior art doughs often have an elastic character which makes their handling difficult, in particular in an industrial plant. The doughs containing the whey according to the invention are easier to pull, blend and smooth.

production of a bread product which is softer than those of the prior art, all else being equal. The softness is an assessment criterion to which the consumer is very sensitive. It is assessed both by the touch and by the taste. Sensory analysis tests carried out on bread products comprising the whey according to the invention, compared with products not containing it, have shown the superiority of the bread products according to the invention compared with those of the prior art in relation to this criterion.

production of a bread product with a better capacity for retaining water, all else being equal. This property manifests itself for the consumer by a less rapid drying of the bread product, in particular when it is exposed to the air.

possibility of preparing a dough free of customary emulsifying agents. It is therefore possible to prepare a bread product from a dough containing, as sole emulsifying agent, the whey according to the invention.

According to an advantageous embodiment of said modified whey, it preferably comprises a quantity of lactose representing 35% by weight of the quantity initially present in the unmodified initial whey.

It will be seen in the examples which follow that these quantities of lactose and of remaining total proteins in the modified whey of the invention are characteristics which make it possible to slow the staling of bread products containing said whey.

The subject of the present invention is also the use of the modified whey of the invention as a bread improver. The modified whey of the invention is effectively used to manufacture in particular industrial breads which exhibit slow staling compared with industrial breads which do not contain the modified whey according to the invention.

Quantities of 0.1 to 0.6%, preferably of 0.2 to 0.6% of modified whey relative to the quantity of flour (w/w), preferably of 0.4%, are preferably added.

The subject of the present invention is additionally a bread product comprising the modified whey according to the invention. Said bread product is advantageously sandwich bread, a genoese, bread with poolish and hamburger-type bread.

According to an advantageous embodiment of said bread product, it additionally comprises at least one of the following additives: lupine flour, amylase or any product derived from the fractionation of milk fat, in particular cholesterol or ultrafiltration retentate of buttermilk.

Advantageously:

hamburger-type bread and sandwich bread with poolish will comprise, in addition to the modified whey according to the invention, lupine flour and an amylase, sandwich bread with poolish will additionally advantageously comprise cholesterol or a buttermilk retentate characterized by a dry extract of about 17%, a content of protein material of about 75% relative to the dry extract, and a fat content of about 10% relative to the dry extract.

The invention will be understood more clearly with the aid of the additional description which follows, which are examples of preparation of the modified whey in accordance with the invention and comparative studies of the staling of various breads, and the accompanying drawings in which.

EXAMPLE 1

Figure 1:
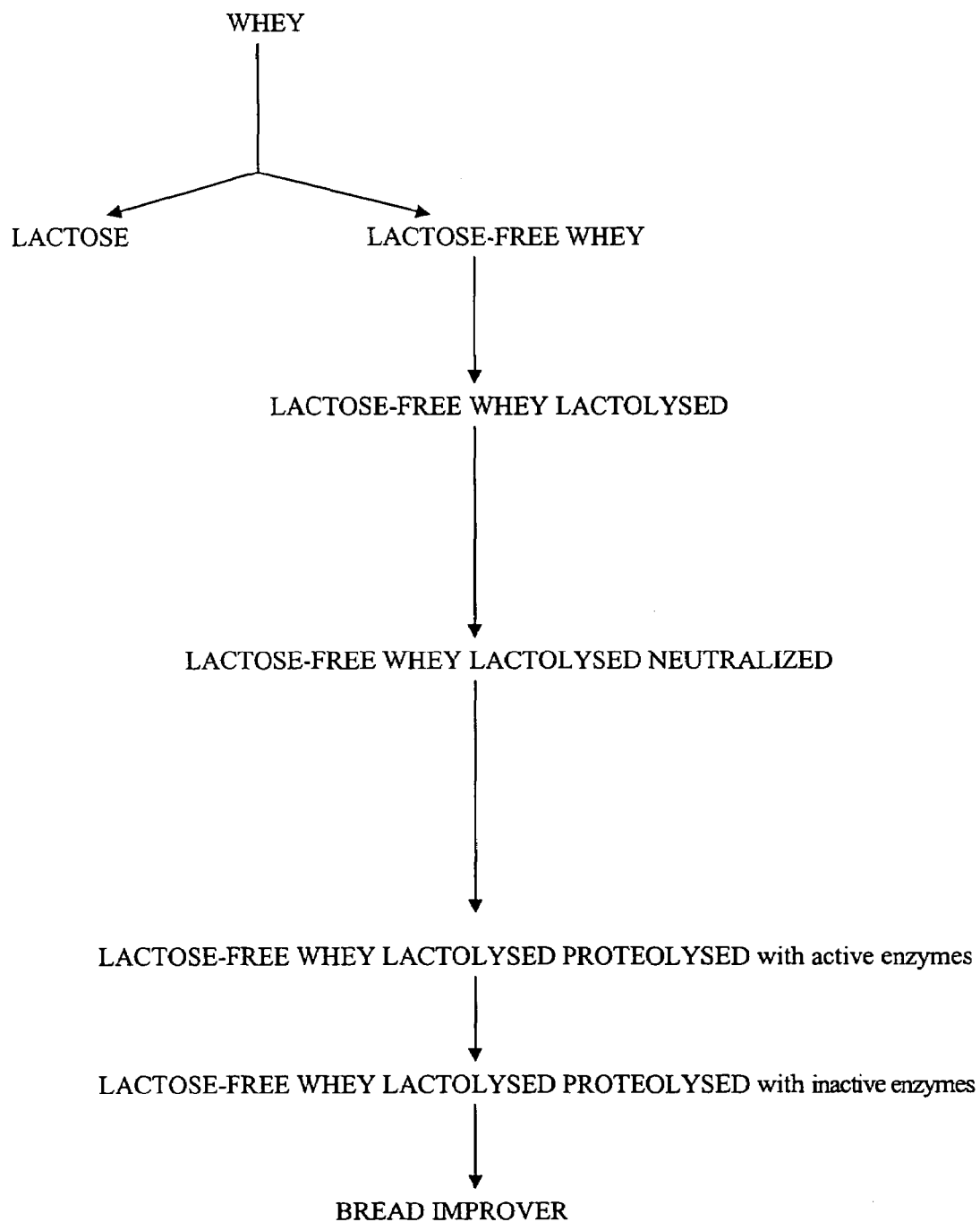
FIG. 1 illustrates the general method according to the invention.
Figure 2:
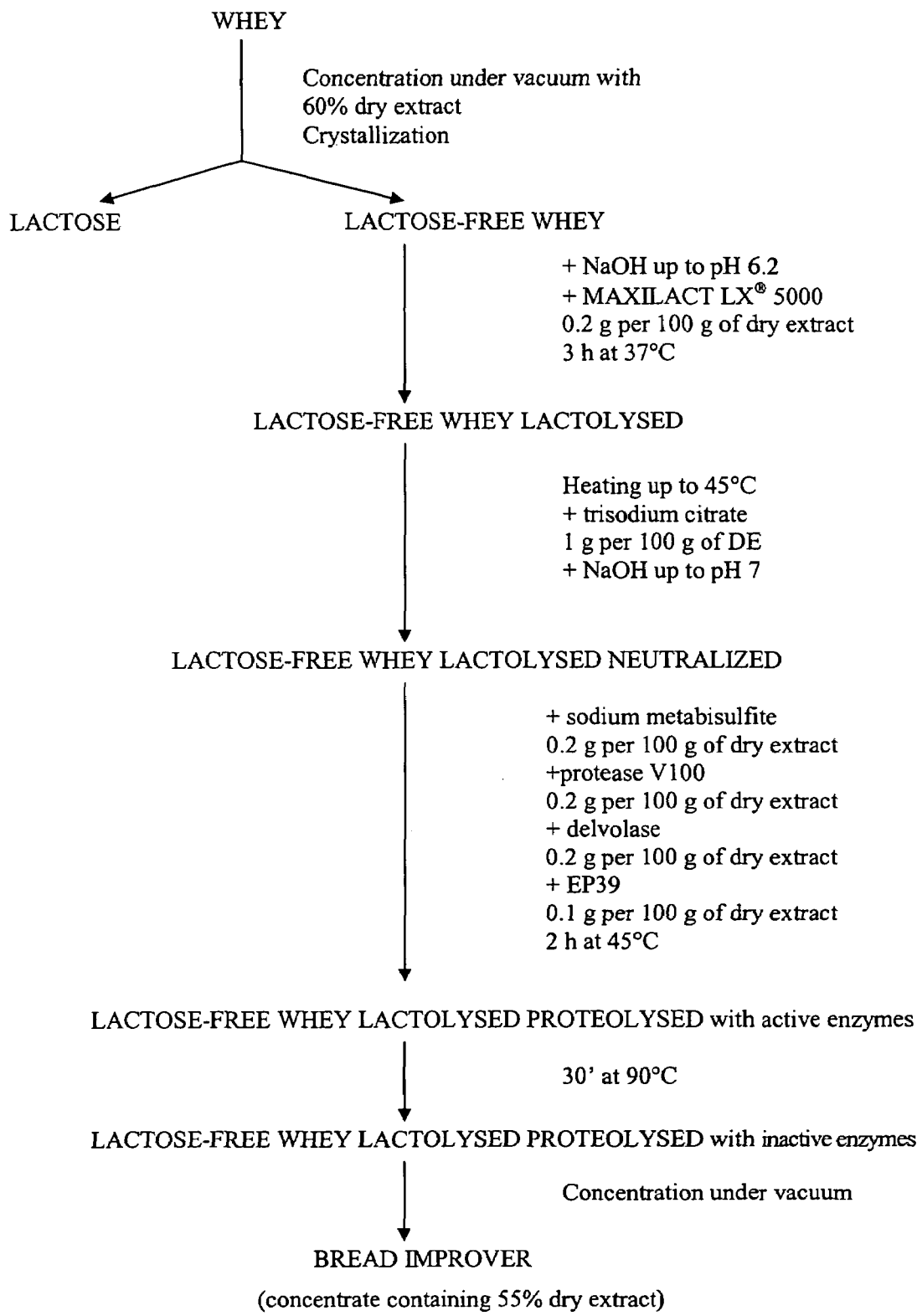
FIG. 2 illustrates a preferred embodiment of the method according to the invention.

Method for Preparing Modified Whey a) Removal of lactose from the whey:

The whey is solubilized by heating to 60–70° C. a whey solution, and then concentrated under vacuum to 60% dry extract, and gently cooled to 4° C. (over 48–72 h) in order to obtain a crystallized product which makes it possible to separate the crystallized lactose from the lactose-free whey.

b) Hydrolysis of the whey obtained in step a):

20 kg of lactose-free whey powder obtained in step a) and containing 26% nitrogenous material are dissolved in 46 liters of water at 60° C. The solution is sterilized by heating for 30 minutes at 90° C. and then cooled to 37° C. and neutralized to pH 6.4 by adding 30% sodium hydroxide. 40 g of lactase (MAXILACT® LX 5000 marketed by DSM) are added to the solution in order to allow the reaction to proceed for 3 h.

c) Pretreatment of the proteins:

The temperature of the medium is then brought to 45° C. and 200 g of trisodium citrate are added. The pH is finally adjusted to 7 with 30% sodium hydroxide.

d) Hydrolysis of the proteins:

40 g of sodium metabisulfite, 40 g of papain (PROTEASE® V100 marketed by DSM), 40 g of alkaline protease from *Bacillus licheniformis* (DELVOLASE® marketed by DSM) and 20 g of fungal protease (Protease M "Amano" marketed by UNIPEX) are added to the reaction medium in order to carry out a hydrolysis for 2 h at 45° C.

e) Inactivation of the enzymes:

At the end of the reaction, the temperature is brought to 90° C. for 30 minutes.

f) Concentration of the modified whey

The medium is cooled to 4° C. before being concentrated by evaporation under vacuum to a dry extract of 55%.

EXAMPLE 2

Sandwich Bread

The product obtained in example 1 is used in a sandwich bread recipe by way of comparison of NOVAMYL® and a control without technological aid:

|  | CONTROL | Trial with Novamyl ® alone | Trial Novamyl ® and modified whey |
|---|---|---|---|
| Flour (g) | 500 | 500 | 500 |
| Water (g) | 250 | 250 | 250 |
| Butter (g) | 100 | 100 | 100 |
| Yeast (g) | 25 | 25 | 25 |
| Sugar (g) | 20 | 20 | 20 |
| Salt (g) | 6 | 6 | 6 |
| Novamyl ® (mg) | 0 | 20 | 2 |
| Concentrated modified whey (g of dry extract) | 0 | 0 | 4 |

The recipe also includes one egg per 500 g of flour.

In order to avoid the development of molds, 2.5 g of calcium propionate are added per 500 g of flour.

Each bread is manufactured from 400 g of dough placed in a mold for 40 minutes of proofing at 35° C. followed by baking for 25 minutes at 230° C. in a hearth-type oven. After baking, the bread is allowed to cool for a few hours at room temperature before being wrapped in plastic.

Random tasting of the products by a panel of 10 tasters after 8 to 15 days of storage in plastic at room temperature showed that the control was judged to be highly staled while the sandwich bread according to the invention preserved its softness even better than the sandwich bread containing only Novamyl®.

EXAMPLE 3

Genoese

The modified whey in accordance with the invention, whose manufacture is described in example 1, is incorporated during the preparation of a genoese: 8 eggs are mixed with 250 g of sugar in a bowl at 30° C. The mixture is beaten for 10 minutes at speed 3 and then for 10 minutes at speed 2 until a ribbon is obtained. 250 g of flour are then carefully added and the whole is placed in a mold and immediately placed in an hearth-type oven at a temperature of 190° C. for 30 minutes of baking.

Various types of genoese were prepared differing in the addition of the following ingredients at the dose of 20 g per kg of flour:

|  | Ingredients |
|---|---|
| CONTROL | none |
| Trial 1 | lactose |
| Trial 2 | unmodified whey |
| Trial 3 | lactose-free whey |
| Trial 4 | modified whey (example 1) in accordance with the invention |

After 13 days of storage, the products were identical as for their taste but differed in their soft appearance in the following decreasing order:

trial 4>trial 3=trial 2=trial 1>control

After 20 days of storage, the product derived from trial 4 remained always the softest.

EXAMPLE 4

Hamburger-type Bread

Hamburger-type bread was manufactured according to the following recipe:

Wheat flour: 2 000 g
Water: 1 160 g
Yeast: 100 g
Sugar: 60 g
Butter: 60 g
Salt: 40 g
Soybean flour: 10 g The whole is kneaded for 20 minutes at the maximum speed in a HOBBART beater with a pig-tail guide. The dough is divided into dough pieces of 110 g and placed in a mold at 25° C. for 1 hour of final proofing (dough rest period preceding baking: the bread fermentation occurs during this period). The dough pieces are finally baked at 240° C. for 12 minutes.

The following trials are distinguishable by the incorporations of ingredients capable of slowing the staling of the product:

| mg of dry extract/kg of flour | CONTROL | Trial 1 | Trial 2 |
|---|---|---|---|
| NOVAMYL ® | 0 | 40 | 4 |
| Modified whey of example 1 | 0 | 0 | 4 000 |

On the 11th day of storage, the hamburger-type bread was randomly examined by a panel of 6 people who gave a score between 1 (staled) and 7 (very soft) to the various products. The total of the scores obtained was:
Control: 11
Trial 1: 29
Trial 2: 33

It therefore seems advantageous to replace most of the Novamyl® which can be incorporated into industrial bread products.

EXAMPLE 5

Sandwich Bread with Poolish

Sandwich bread with poolish was prepared according to the following recipe:
Poolish (hydrated flour comprising yeast)
Poolish:
Fine wheat flour: 750 g
Water: 60 g
Yeast: 3.7 g
Fermented for 16 h at 20° C.
Preparation of the sandwich bread
Poolish: 1 353.7 g
Fine wheat flour: 1 500 g
Water: 818 g
Lard: 225 g
Yeast: 86 g
Sugar: 67 g
Salt: 45 g
Soybean flour: 33.8 g
Calcium propionate: 3.4 g The doughs obtained are placed in the container for 1 h of first rising: dough rest period which follows kneading and allows a first yeast fermentation stage and structuring of the dough; 400 g dough pieces are weighed and slightly raised for an expansion of 15 minutes. They are then placed in a mold for 1.5 h of final proofing at 25° C. and in order to obtain 85% relative humidity. The baking is finally carried out in an open mold at 230° C. for 25 minutes. The unmolding is carried out immediately after baking for a cooling of 3 h.

The following trials differed from the previous ones in the incorporation into the portion free of poolish of ingredients capable of slowing the staling of the bread.

| mg of dry extract/kg of flour | CONTROL | Trial 1 | Trial 2 |
|---|---|---|---|
| NOVAMYL ® | 0 | 40 | 4 |
| Modified whey of example 1 | 0 | 0 | 4 000 |

The modified whey is that described in example 1.

After 18 days of storage, the control was completely staled whereas the bread of trial 1 and trial 2 retained all their softness.

EXAMPLE 6

Hamburger-type Bread

Hamburger-type bread was manufactured as described in example 4.

The following trials were carried out which differ in the incorporation of ingredients capable of slowing the staling of the product:

| mg of dry extract/kg of flour | CONTROL | Trial 1 | Trial 2 |
|---|---|---|---|
| NOVAMYL ® | 0 | 40 | 0 |
| Modified whey of example 1 | 0 | 0 | 4 000 |
| Lupine flour | 0 | 0 | 3 000 |
| BREWERS AMYLIQ ® | 0 | 0 | 0.05 |

BREWERS AMYLIQ® is a bacterial amylase derived from *Bacillus amyloliquefaciens* and is marketed by DSM France.

On the 17th day of storage, the hamburger-type bread was randomly examined by a panel of 6 people who had to give a score between 1 (staled) and 7 (very soft) to the various products. The total of the scores obtained was:
Control: 11
Trial 1: 30
Trial 2: 22

It therefore seems possible to slow the staling of hamburger-type bread by a formulation free of NOVAMYL® but containing on the other hand modified whey as described in the present invention.

EXAMPLE 7

Sandwich Bread with Poolish

Sandwich bread with poolish was manufactured as described in example 5. The following trials were carried out which differ in the incorporation of ingredients capable of slowing the staling of the product:

| mg of dry extract/kg of flour | CONTROL | Trial 1 | Trial 2 |
|---|---|---|---|
| NOVAMYL ® | 0 | 40 | 0 |
| Modified whey of example 1 | 0 | 0 | 4 000 |
| Lupine flour | 0 | 0 | 3 000 |
| BREWERS AMYLIQ ® | 0 | 0 | 0.05 |

On the 14th day of storage, the bread was randomly examined by a panel of 6 people who had to give a score between 1 (staled) and 7 (very soft) to the various products. The total of the scores obtained was:
Control: 12
Trial 1: 35
Trial 2: 26

It therefore seems possible to slow the staling of this type of bread by a formulation free of NOVAMYL® but comprising on the other hand modified whey in accordance with the invention.

EXAMPLE 8

Sandwich Bread with Poolish

Sandwich bread with poolish was manufactured as described in example 5. The following trials were carried out which differ in the incorporation of ingredients capable of slowing the staling of the product:

| mg of dry extract/kg of flour | Trial CONTROL | Trial 1 | Trial 2 | Trial 3 | Trial 4 | Trial 5 |
|---|---|---|---|---|---|---|
| NOVAMYL ® | 0 | 40 | 0 | 0 | 0 | 0 |
| Modified whey of example 1 | 0 | 0 | 4 000 | 4 000 | 4 000 | 4 000 |
| Lupine flour | 0 | 0 | 3 000 | 3 000 | 3 000 | 3 000 |
| BREWERS AMYLIQ ® | 0 | 0 | 0.05 | 0.05 | 0.05 | 0.05 |
| Cholesterol | 0 | 0 | 0 | 1 000 | 5 000 | 20 000 |

The cholesterol is extracted from milk and is marketed by the company CORMAN (Belgium).

On the 7th day of storage, the bread was randomly examined by a panel of 6 people who had to give a score between 1 (staled) and 7 (very soft) to the various products. The total of the scores obtained was:

Control: 20
Trial 1: 22
Trial 2: 17
Trial 3: 23
Trial 4: 27
Trial 5: 8

It therefore seems possible to slow the staling of this type of bread by a formulation free of NOVAMYL®, with an optimum amount of cholesterol (between 1 and 5 g per kg of flour), but comprising on the other hand modified whey in accordance with the invention.

EXAMPLE 9

Sandwich Bread with Poolish

Sandwich bread with poolish was manufactured as described in example 5. The following trials were carried out which differ in the incorporation of ingredients capable of slowing the staling of the product:

| mg of dry extract/kg of flour | CONTROL | Trial 1 | Trial 2 | Trial 3 | Trial 4 | Trial 5 |
|---|---|---|---|---|---|---|
| NOVAMYL ® | 0 | 40 | 0 | 0 | 0 | 0 |
| Modified whey of example 1 | 0 | 0 | 5 000 | 5 000 | 5 000 | 5 000 |
| METARIN CP ® | 0 | 0 | 40 | 0 | 40 | 0 |
| BREWERS AMYLIQ ® | 0 | 0 | 0.2 | 0 | 0 | 0.2 |
| UF/DF retentate of buttermilk | 0 | 0 | 0 | 4 000 | 0% | 4 000 |

The UF/DF retentate of buttermilk is obtained from pasteurized and ultrafiltered sweet buttermilk at 54° C. on an ORELIS® ultrafiltration plant equipped with membranes having a 10 kD cut-off by producing a volume concentration factor of 5.7, followed by diafiltration to achieve a final volume concentration factor of 7.2. The retentate obtained is characterized by a dry extract of 17.4%, a content of protein material of 75% on a dry extract basis, and a fat content of 9% on a dry extract basis.

On the 17th day of storage, the bread was examined as for the number of soft slices, the slice number starting from which the softness is perceptible, and the classification of the central slices by intensity of softness. The result is the following classification:

trial 3>trial 2>trial 1>control>trial 5>trial 4

It therefore seems possible to slow the staling of this type of bread by a formulation free of NOVAMYL®, but comprising on the other hand modified whey in accordance with the invention and supplemented with emulsifiers of various origins.

EXAMPLE 10

Effect of the Whey According to the Invention on the Water-retaining Capacity and the Softness The capacity of the modified whey according to the invention to retain water and consequently to become more hydrated in the kneader is demonstrated in the following example:

| TRIAL | WATER | FLOUR | MODIFIED WHEY |
|---|---|---|---|
| 1 | 204 g | 375 g | 0 g |
| 2 | 230 g | 350 g | 1.8 g |

The hydration in the kneader is increased from 54.4 to 65.7% in the presence of 0.5% of modified whey according to the invention, giving sandwich bread having the following moisture values:

| | MOISTURE | | |
|---|---|---|---|
| TRIAL | from the oven | at 8 days | at 15 days |
| 1 | 20.2% | 18.5% | 17.5% |
| 2 | 21.9% | 20.2% | 19.1% | and a softness judged to be better for trial 2 than for trial 1. This represents a saving on flour of 6.5% for manufacturing a finished product judged to be better.

EXAMPLE 11

Effect of the Modified Whey According to the Invention on the Smoothing of the Doughs The capacity of the modified whey according to the invention to smooth the doughs is demonstrated by the effect of the product in a CHOPIN alveograph on bread flour:

|  | P | G | W | P/L |
| --- | --- | --- | --- | --- |
| CONTROL FLOUR | 60 | 26.0 | 222 | 0.44 |
| CONTROL + 1% of modified whey according to the invention | 50 | 28.1 | 175 | 0.32 |

The parameters P, G, W and L measured according to the NF iso 5530-4 standard represent the following effects on the dough:

P represents the maximum pressure of an air bubble contained in the dough,
G represents the rise in the dough and represents its extensibility,
W represents the work of resistance of the dough to deformation,
L is defined by $G=2.22\sqrt{L}$ The variation of the parameters P and W (downward), G (upward) is typical of an effect of dough softening as commonly obtained with ingredients such as deactivated yeasts, cysteine and metabisulfite.

EXAMPLE 12

Replacement of an Emulsifier by Whey Combined with a Fat

The whey, modified according to the invention and combined with a buttermilk (BAEF marketed by the company CORMAN (Belgium)) was introduced with a bread improver comprising broad bean flour (5 g per kg of flour), the emulsifier E471 (3.5 g per kg of flour), fungal amylases and hemicellulases (0.15 g per kg of flour) and ascorbic acid (0.1 g per kg of flour) containing or otherwise the emulsifier E481 for the improver formulas:

| TRIAL | E481 | Modified whey according to the invention | BAEF |
| --- | --- | --- | --- |
| 1 | 1.5 g | 7 g | 1.4 g |
| 2 | 0 | 7 g | 1.4 g |

| | FIRMNESS | |
| --- | --- | --- |
| TRIAL | at 7 days | at 14 days |
| 1 | 547 | 796 |
| 2 | 563 | 720 |

The measurement of firmness, determined using a STEVENS penetrometer, is given in newtons.

The results show that the use of the modified whey according to the invention in combination with buttermilk advantageously makes it possible to dispense with the emulsfier E481 commonly used in industrial sandwich bread for slowing the increase in the firmness of sandwich bread during the first 10 days of storage.

The ivention claimed is:

1. A method for preparing a modified whey, comprising:
    a) removal of lactose from an unmodified initial whey by evaporation of the whey, to crystallize the lactose and to form a concentrated whey comprising from 55 to 70% dry matter,
    b) hydrolysis of the whey formed in a) with one or more lactases to reduce the lactose level to between 10 and 50% by weight of the quantity of lactose initially present in the unmodified initial whey,
    c) pretreatment of the proteins contained in the reduced lactose whey formed in b) by adding a calcium trap to said whey, in the hot state and at a substantially neutral pH,
    d) hydrolysis, in the hot state, of the pretreated proteins from c) by at least one endopeptidase, at least one exopeptidase and at least one molecule capable of cutting the disulfide bridges until a level of total proteins is at most 80% by weight of the initial weight of proteins present in the unmodified initial whey; and
    e) inactivation of all the enzymes present in the whey formed in d).

2. The method as claimed in claim 1, wherein the hydrolysis b) is carried out at 37° C., in the presence of an acid lactase which has an optimum activity at a pH of between 3 and 5 or in the presence of a neutral lactase which has an optimum activity at a pH of between 5 and 7.

3. The method as claimed in claim 2, wherein the quantity of lactase is from 0.1 to 0.5 g per 100 g of dry matter.

4. The method as claimed in claim 1, wherein the pretreatment of the proteins c) is carried out at a temperature between 40° C. and 50° C. and at a pH between 6.5 and 7.5.

5. The method as claimed in claim 1, wherein the calcium trap in c) is present in a quantity of 1% dry extract and, is selected from the group consisting of disodium citrate, sodium lactate and a polyphosphate.

6. The method at claimed in claim1, wherein the hydrolysis d) is carried out at a temperature between 35° C. and 60° C., by
    at least one endopeptidase selected from the group consisting of a neutrase, pancreatin, delvolase, alkaline protease derived from *Bacillus licheniformis*,papain, protease V100 and a neutral protease from the genus *Aspergillus* selected from the group consisting of *niger, oryzae, sojae, melleus* and *wentii*,
    at least one exopeptidase of the genus *Aspergillus* seleted from the group consisting of *niger, oryzae, sojae, melleus* and *wentii*, and
    at least one molecule capable of cutting the disulfide bridge, selected from the group consisting of sodium metabisulfite, cysteine and a glutathion-rich yeast extract.

7. The method as claimed in claim 1, wherein the temperature and the duration of e) are 90° C. for 30 minutes.

8. The method as claimed in claim 1, further comprising
    f) concentrating the modified whey from e) to form a concentrate 50–60% dry extract.

9. A modified whey obtained by the method as claimed in claim 1, comprising 10 and 50% by weight of lactose based on the quantity by weight initially present and a quantity of total proteins representing at most 80% by weight of the quantity by weight of proteins initially present.

10. The modified whey as claimed in claim 9, in liquid form, in the form of a concentrate or of a dry powder.

11. The modified whey as claimed in claim 9 in the form of a concentrate containing 50–70% dry extract.

12. The modified whey as claimed in claim 9, comprising 35% by weight of lactose based on the initial lactose present in the unmodified initial whey.

13. A bread improver comprising the modified whey of claim 9.

14. An industrial bread product comprising the modified whey as claimed in claim 9 in a quantity of 0.1 to 0.6% by weight relative to the quantity of flour.

15. The bread product as claimed in claim 14 that is free of any other emulsifying agent.

16. The method as claimed in claim 1, wherein the hydrolysis of the whey is carried out at a pH between 3 and 7 and at a temperature of less than or equal to 40° C.

17. The method as claimed in claim 2, comprising carrying out the hydrolysis in the presence of an acid lactase at a pH of 4.

18. The method as claimed in claim 2, comprising carrying out the hydrolysis in the presence of a neutral lactase having an optimum activity at a pH of 6.3.

19. The method as claimed in claim 4, wherein the pH is 7.

20. The method as claimed in claim 6, wherein the temperature is 45° C.

21. The method as claimed in claim 8, wherein the concentrate has 55% dry extract.

22. A method comprising:
mixing the modified whey as claimed in claim 9 with at least flour to form a bread dough with improved smoothing as compared to a bread dough without said modified whey.

23. A method comprising:
mixing the modified whey as claimed in claim 9 with at least flour to form a bread dough with improved softness as compared to a bread dough without said modified whey.

24. A method comprising:
mixing the modified whey as claimed in claim 9 with at least flour to form a bread dough having improved water-retaining capacity as compared to a bread dough without said modified whey.

25. A bread product comprising the modified whey as claimed in claim 9.

26. The bread product as claimed in claim 25, further comprising at least one of lupine flour, amylase or any product derived from the fractionation of milk fat.

27. The bread product as claimed in claim 26, further comprising at least one of cholesterol or an ultrafiltration retentate of buttermilk.

* * * * *